United States Patent [19]

Hoeks

[11] Patent Number: 5,412,707
[45] Date of Patent: May 2, 1995

[54] X-RAY EXAMINATION APPARATUS AND ARRANGEMENT FOR REMOTE-CONTROLLED POSITION INDICATION

[75] Inventor: Antonius J. L. M. Hoeks, Breugel, Netherlands

[73] Assignee: U.S. Philips Corporation, New York, N.Y.

[21] Appl. No.: 259,277

[22] Filed: Jun. 13, 1994

Related U.S. Application Data

[63] Continuation of Ser. No. 82,186, Jun. 24, 1993.

[30] Foreign Application Priority Data

Jun. 25, 1992 [EP] European Pat. Off. ........... 92201870

[51] Int. Cl.⁶ .............................................. G03B 42/02
[52] U.S. Cl. ..................................... 378/165; 378/162
[58] Field of Search ........................ 378/162, 165, 167

[56] References Cited

U.S. PATENT DOCUMENTS 4,860,330  8/1989  Strömmer et al. ................... 378/165

FOREIGN PATENT DOCUMENTS 1270680  7/1961  France .
2948109  6/1981  Germany .
3228577  2/1984  Germany .
0008135  1/1987  Japan .................. 378/165

Primary Examiner—David P. Porta
Attorney, Agent, or Firm—Jack D. Slobod

[57] ABSTRACT

Information on positioning of a patient during x-ray examination is provided by imaging a marker, notably a lead-letter, simultaneously with imaging a patient. Remote-controlled markers are provided attached to separate moveable flat frames. The use of a flat frame makes possible to incorporate an arrangement for remote-controlled position and/or orientation, within the serial film changer without increasing required vertical space. Thus comfortable and easy access for a patient onto the patient table is provided. The motion of relevant frames along guide rails is performed by means of a system of motors, belts or chains and pulleys. The motors are controlled by means of potentiometers and a micro-processor that supplies signals in correspondence with a required motion of a relevant frame. The motors are positioned within the serial film changer and aside of the patient support table. As a consequence restriction of the longitudinal motion of the patient support table is avoided. By means of a system of levers and switches collision of frames with the outer casing of the serial film changer is avoided. Further safeguarding against unintentionally imaging markers is provided by means of a system of levers and switches that transmit a signal to the micro-processor whenever markers are positioned in a predetermined position in which they are outside the x-ray beam.

8 Claims, 2 Drawing Sheets

X-RAY EXAMINATION APPARATUS AND ARRANGEMENT FOR REMOTE-CONTROLLED POSITION INDICATION

This is a continuation of application Ser. No. 08/082,186, filed Jun. 24, 1993.

BACKGROUND OF THE INVENTION

1. Field of the Invention

The invention pertains to an x-ray examination apparatus comprising an arrangement for remote-controlled position indication by placing a marker in a field of x-rays. The invention also relates to an arrangement for providing remote-controlled position indication on x-ray images suitable for use in such an x-ray examination apparatus.

2. Description of the Related Art

An x-ray examination apparatus of said kind is known from the German *Patentschrift* DE 32 28 577.

For performing appropriate medical treatment on a basis of a diagnosis obtained by using an x-ray image, it is desirable that information on orientation and/or position of a patient during x-ray examination is recorded on x-ray film together with the x-ray image. This is achieved by imaging relevant markers, e.g. lead-letters, which are at option placed in the x-ray beam. In the x-ray examination apparatus as described in the cited reference, information on the position and the orientation of a patient during examination is provided on x-ray images by imaging lead-letters simultaneously with imaging the patient. In the x-ray examination apparatus according to the cited reference, a disc containing a plurality of different lead-letters, each of them corresponding to one of a plurality of patient positions and/or orientations, is rotatably attached to an x-ray shutter. Implicitly it is obvious, that the x-ray examination apparatus described in the cited reference, comprises an x-ray detector consisting of a film holder containing x-ray sensitive film-material. A relevant choice of letters to be imaged on x-ray images can be made by suitable rotation of the disc. The disc is driven by an arrangement of cables, pulleys, a winch and a motor; said arrangement being placed in an extension of the film holder along a longitudinal direction of the patient table. In the arrangement as described in the cited reference, the motor for driving the disc is positioned beneath the patient table, so that for accommodating space for incorporating the motor, the patient table must be positioned at a sufficiently large height above a floor on which the x-ray examination apparatus is installed.

SUMMARY OF THE INVENTION

It is inter alia an object of the invention to provide an arrangement for remote-controlled position indication on x-ray images, for an x-ray examination apparatus that is comfortably accessible for patients and that is adequate for a variety of image formats.

To achieve this, an x-ray examination apparatus in accordance with the invention is characterized in that said marker is mounted on a flat frame being moveable in a plane parallel to a predetermined image plane.

The extent to which patients have comfortable and easy access to an x-ray examination apparatus is substantially determined by the height of a patient table above the floor. Comfort and easy access can be substantially increased by decreasing the height of the patient table above the floor. For providing x-ray images on film, an x-ray examination apparatus incorporates a film holder for containing x-ray sensitive film-material for x-ray detection, notably in the form of a serial film changer, placed below the patient table. In order to substantially avoid that vertical space is needed for incorporating an arrangement for positioning said markers within the serial film changer, the required height for incorporating said arrangement within the serial film changer is limited to the thickness of the employed markers. By mounting markers on a flat frame, the thickness of said frame does not have to exceed the thickness of said markers. Therefore an arrangement for remote controlled position indication can be incorporated within the serial film changer without increasing its height.

Having markers, notably lead-letters, attached to separate frame parts, rather than to any other moveable parts of an x-ray examination apparatus, such as e.g. to x-ray shutters that are moveable in correspondence to film cassette formats, there is provided an option to position lead-letters independently of positions of any other moveable parts of an x-ray examination apparatus. Therefore, lead-letters can be positioned more freely, so as to image a lead-letter in an x-ray image without a relevant lead-letter compromising visibility of relevant information contained in the x-ray image.

A preferred embodiment of an x-ray examination apparatus in accordance with the invention is characterized in that said frame is driven by drive means positioned aside of said patient table.

In an x-ray examination apparatus in accordance with this preferred embodiment the dimension in a longitudinal direction of the patient table of the serial film changer is reduced as compared to the corresponding dimension in an x-ray examination apparatus as described in the cited reference. Therefore an x-ray examination in accordance with the invention, a longitudinally stroke over which the patient table can be moved is increased. As a consequence an x-ray examination procedure by means of an x-ray examination apparatus in accordance with the invention is substantially facilitated. A motor for driving relevant markers to relevant positions usually has dimensions that exceed the thickness of the markers. However, in an x-ray examination apparatus in accordance with the invention, it is achieved that no increase of vertical height of the serial film changer is needed by positioning one or several motors aside of the patient table.

A further preferred embodiment of an x-ray examination apparatus in accordance with the invention is characterized in that said arrangement comprises control means for controlling the position of said marker.

In medical x-ray examination procedures it is customary to employ various formats of film cassettes in dependence of a type of x-ray examination at issue. In an x-ray examination apparatus in accordance with the invention, the markers for providing patient position and/or orientation information on x-ray images can be positioned so that said patient position and/or orientation information is imaged in a region of x-ray images on film where said information does not interfere with relevant (medical) image information. Upon insertion of a film cassette in the serial film changer a format of said film cassette is detected by means of sensors and a microprocessor and subsequently control signals are produced by the microprocessor for controlling motors driving relevant frames having markers attached into desired positions.

A further preferred embodiment of an x-ray examination apparatus in accordance with the invention is characterized in that said arrangement comprises a system of levers and switches for preventing collision of said frame with other parts of the apparatus.

Should a frame collide with any other part of the arrangement, it is desirable that a relevant motor is switched off. To that end a system of switches and levers is provided. In case of a collision being imminent, a relevant switch is operated by a relevant lever, so as to interrupt power supply to a relevant motor.

A further preferred embodiment of an x-ray examination apparatus in accordance with the invention is characterized in that said arrangement comprises a system of levers and switches for producing a signal representing a predetermined position of said marker.

For adding to reliability of patient position and/or orientation indication on x-ray images, a safeguarding means is provided. In order to avoid unintentionally imaging of lead-letters, it is important that it is ascertained that indeed no lead-letters are imaged when it is intended not to image any lead-letters. To that end a further system of levers and switches is provided, for generating a signal pertaining to lead-letters being in positions where they cannot be imaged during x-ray exposure. A further control signal is then transmitted to the microprocessor and compared to positioning information concerning relevant frames supplied by the micro-processor. Whenever a discrepancy occurs between said control signal and information supplied by the microprocessor, then a warning signal is by the microprocessor and supplied to a control means of the x-ray examination apparatus thereby informing an operator performing an x-ray examination that position and/or orientation indication imaged on x-ray images cannot be relied upon.

An arrangement for remote-controlled position indication by placing a marker in a field of x-rays suitable for use in an x-ray examination apparatus in accordance with the invention, preferably comprises a marker mounted on a flat frame being moveable in a plane parallel to a predetermined image plane and drive means for moving said marker symbol being attached to said moveable frames, said drive means being positioned aside of a patient table when the arrangement is incorporated in an x-ray examination apparatus in accordance with the invention.

These and other aspects of the invention will become apparent and will be elucidated with reference to the embodiments described hereinafter with reference to the accompanying drawings.

DETAILED DESCRIPTION OF THE PREFERRED EMBODIMENT

Figure 1:
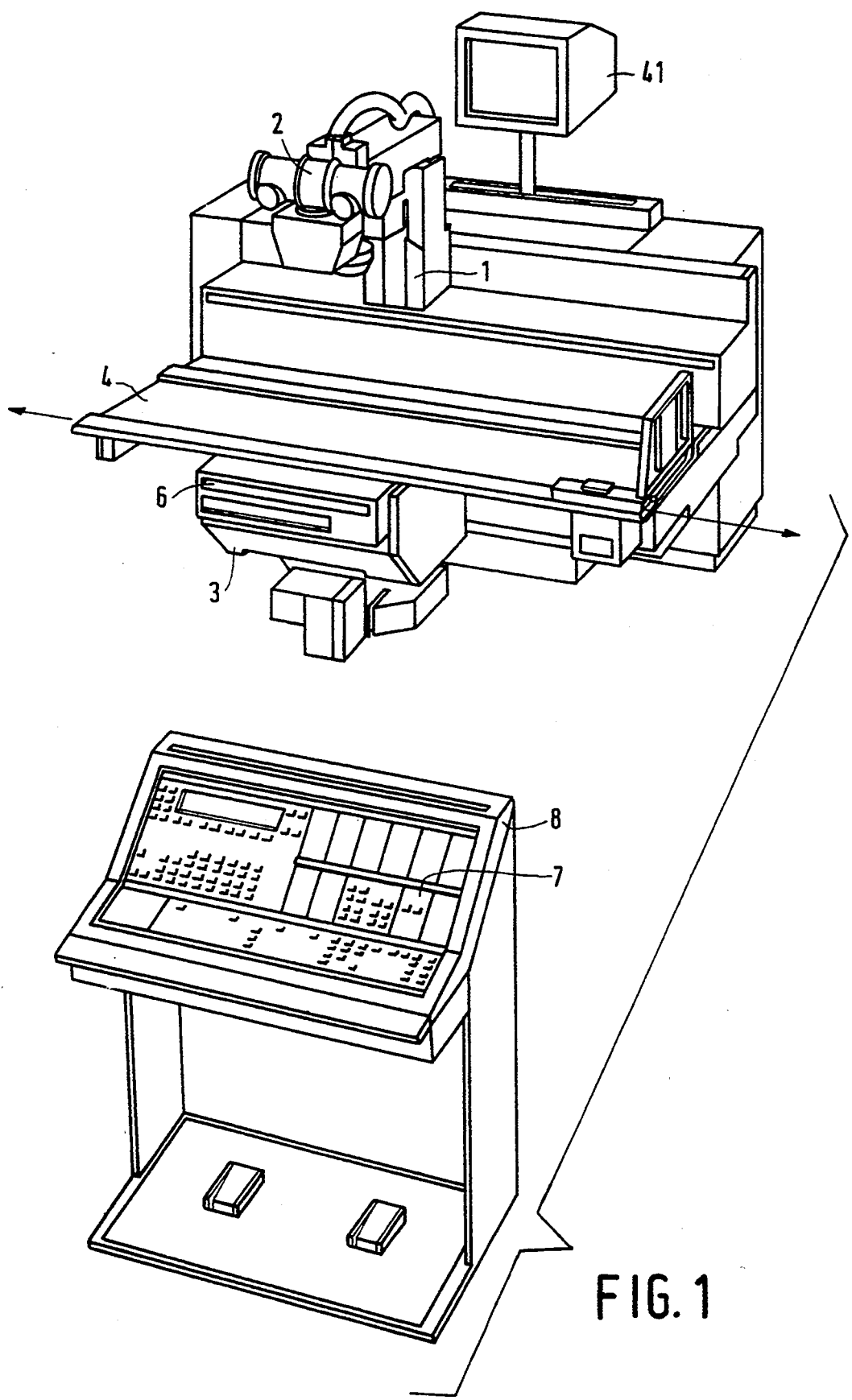
FIG. 1 shows a side elevation of an x-ray examination apparatus comprising a serial film changer positioned underneath a patient support table.

An x-ray examination apparatus as shown in FIG. 1 comprises a carrier 1 supporting an x-my source 2 for generating an x-ray beam. An x-ray detector 3, having the form of a serial film changer is facing the x-ray source. A table 4 for supporting a patient is situated between the x-ray source and the x-ray detector. An arrangement 5 for remote-controlled position indication on x-ray images produced by an x-ray examination apparatus in accordance with the invention is incorporated in the serial film changer. The arrangement 5 is not visible in FIG. 1, but will be further discussed in the sequel with reference to FIG. 2. For producing x-ray images on hard-copy, notably x-ray film, film cassettes are to be inserted into a slot 6 of the serial film changer. The image plane is then formed by the film that is incorporated in the film cassette. The side of the serial film changer having the slot will be designated hereinafter as the front side of the serial film changer; correspondingly, the side of the serial film changer opposite said front side will be referred to hereinafter as the rear side of the serial film changer. The table supporting the patient is moveable inter alia along the directions of the arrows. The x-ray examination apparatus can be operated by means of a control panel 7 on a control desk 8.

Figure 2:
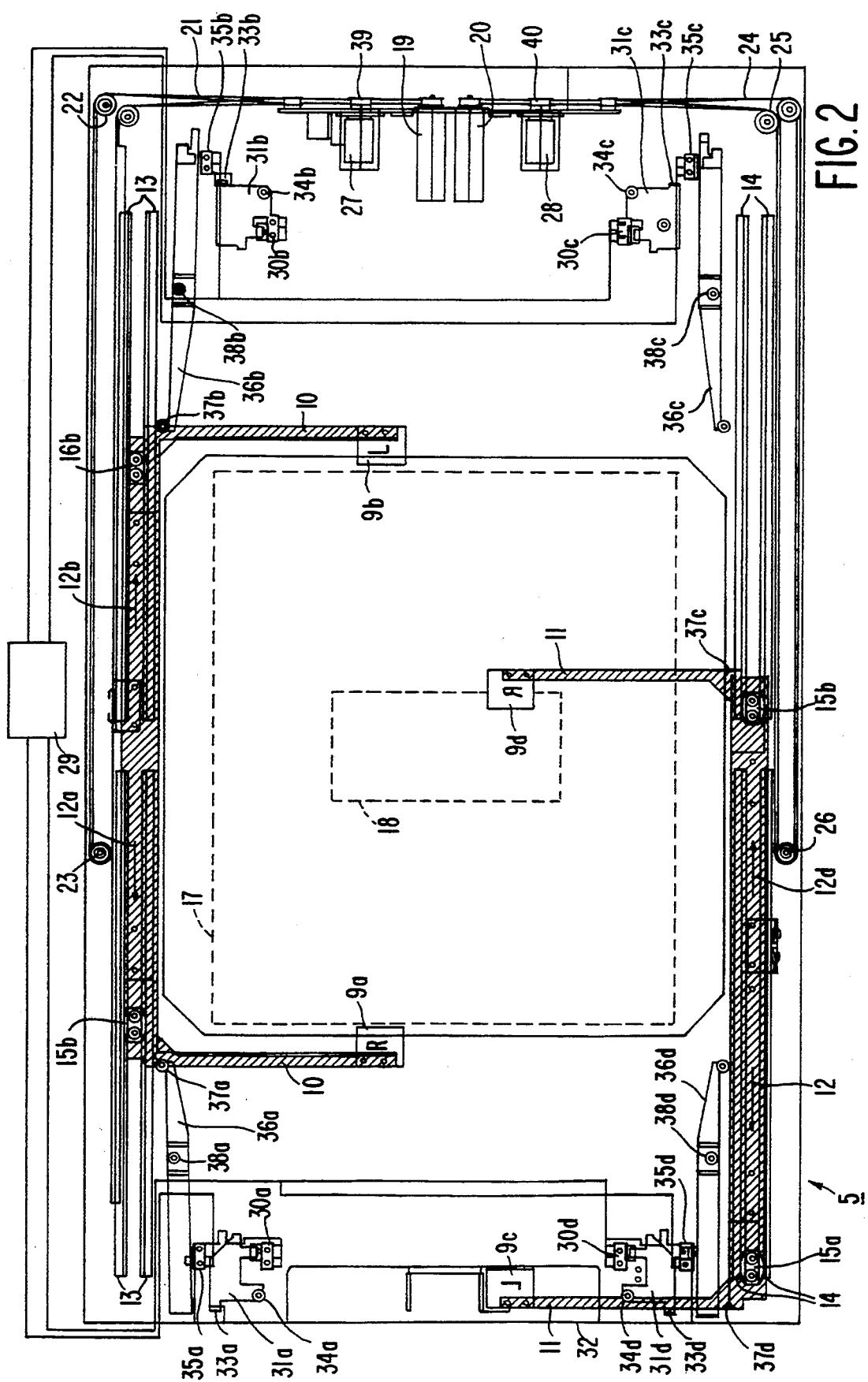
FIG. 2 shows a plan view of an arrangement for remote- controlled position indication on x-ray images in accordance with the invention.

FIG. 2 shows a plan view of an arrangement 5 for remote-controlled patient position and/or orientation indication on x-ray images in accordance with the invention. Position indication is performed by imaging appropriate markers consisting of lead-letters together with the imaging of a patient. A set of four lead-letters 9a–d are provided. A first pair consisting of 9a and 9b is attached to a first moveable frame 10 and a second pair consisting of 9c and 9d is attached to a second moveable frame 11. The first frame 10 and the second frame 11 are moveable in the directions indicated by arrows 12a and 12b, and by arrows 12c and 12d, respectively. The arrangement 5 for remote controlled position indication is incorporated in the serial film changer in such a way that the plane in which the markers 9a–d are moveable is substantially parallel to a surface of the patient table 4, and the motors for driving the frames are placed at the rear end of the serial film changer. To facilitate motion of the frames sets of guide rails 13 and 14 are provided and the frame part 9 is provided with guide means 15a and 16a and frame part 10 is provided with guide means 15b and 16b. The frame part 10 is shown in FIG. 2 positioned in a standby position. In this standby position neither lead-letter 9a, nor lead-letter 9b is imaged for any film cassette format that is suitable for use in an x-ray examination apparatus in accordance with the invention. A contour indicating an outer edge of a film cassette of a largest format suitable for use in an x-ray examination apparatus in accordance with the invention is shown in FIG. 2 by way of the dashed contour 17. A contour indicating the outer edge of a film cassette of a smallest format suitable for use in an x-ray examination apparatus in accordance with the invention is shown in FIG. 2 by way of the dashed contour 18. Frame 11 is shown in FIG. 2 positioned in an exposure position. In this exposure position lead-letter 9d is imaged on an x-ray image made employing a film cassette of the smallest format suitable for use in an x-ray examination apparatus in accordance with the invention.

Motors are provided as drive means for displacing frames and lead-letter attached to them. The motion of frames and lead-letters attached to them is driven by motors. A first motor 19 is provided for driving the motion of frame 10 along guide rails 13, by means of a belt 21 and systems of pulleys 22 and 23. A second motor 20 is provided for driving the motion of frame 11 along guide rails 14, by means of a belt 24 and systems of pulleys 25 and 26. For controlling the motion of frame 10 control means comprising first potentiometer 27 is provided that is driven by the motor 19 and the belt 20. For controlling the motion of frame 11 control means comprising a second potentiometer 28 is provided that is driven by the motor 20 and the belt 24. Signals in correspondence with a required number of revolutions of motor 19 and of motor 20, respectively, the required number of revolutions of said motors being in correspondence with a required distance over which any of the frame parts 10 or 11 is required to move, are provided by a micro-processor unit 29; said signals being supplied by the micro-processor unit to a relevant potentiometer.

To stop relevant motors when any one of the frames 10 or 11 arrives at a respective end position, a system of switches 30a–d together with levers 31a–d is provided. When e.g. frame part 11 arrives at an end position for lead-letter 9c, i.e., as shown in FIG. 2, frame part 11 cannot be moved further in the direction of arrow 12c because the frame part 11 would then collide with the outer casing 32 of the serial film changer, then switch 30c is opened by means of the lever 31c. Lever 31c comprises a cam 33c extending in a direction perpendicular to the plane of the drawing of FIG. 2. When frame part 11 reaches an end position for lead-letter 9c, then frame part 11 pushes against the cam 33c, so as to rotate the lever 31c around a centre of rotation 34c. Similarly, switches 30a, 30b and 30d, respectively, are operated by means of levers 31a, 31b, and 31d, having cams 33a, 33b and 33d, respectively. When frame part 11 arrives at an end position for lead-letter 9d, i.e. frame part 11 cannot be moved further in the direction of arrow 12d because the frame part 11 would then collide with the outer casing 32 of the serial film changer, then switch 30d is opened by means of the lever 31d. Lever 31d comprises a cam 33d extending in a direction perpendicular to the plane of the drawing of FIG. 2. When frame part 11 reaches an end position for lead-letter 9d, then frame part 11 pushes against the cam 33d, so as to rotate the lever 31d around a centre of rotation 34d. When frame part 11 arrives at an end position for lead-letter 9a, or 9b, i.e. frame part 11 cannot be moved further in the direction of arrow 12a or 12b, respectively, because the frame part 11 would then collide with the outer casing 32 of the serial film changer, then switch 30a or 30b, respectively, is opened by means of lever 31a, or lever 31b, respectively. Lever 31a comprises a cam 33a extending in a direction perpendicular to the plane of the drawing of FIG. 2. Lever 31b, comprises a cam 33b extending in a direction perpendicular to the plane of the drawing of FIG. 2. When frame part 11 reaches an end position for lead-letter 9a, or lead-letter 9b, respectively, then frame part 11 pushes against the cam 33a, or 33b, respectively, so as to rotate the lever 31a, or lever 31b, respectively, around a centre of rotation 34a, or 34b, respectively.

In order to avoid that lead-letters are unintentionally imaged, it is important that it is ascertained that indeed no lead-letter is imaged when it is intended not to image any lead letter. To that end a safeguarding means comprising a further system of switches 35a–d and levers 36a–d are provided. The frame part 10 is provided with slants 37a and 37b for operating levers 36a and 36b, respectively. By rotation of said levers around centres of rotation 38a and 38b, respectively, said levers operate switches 35a, and 35b, respectively. Whenever frame part 10 is in a standby position, as shown in FIG. 2, then both switches 35a and 35b are closed so as to transmit to the micro-processor unit 29, a signal pertaining to frame part 10 being in a standby position. The frame part 11 is provided with slants 37c and 37d for operating levers 36c and 36d, respectively. By rotation of said levers around centres of rotation 38c and 38d, respectively, said levers operate switches 35c, and 35d, respectively. Whenever frame part 11 is in a standby position, then both switches 35c and 35d are closed so as to transmit a signal to the micro-processor pertaining to frame part 11 being in a standby position. The positions of frames 10 and 11 are also controlled by means of the potentiometers 27 and 28, respectively. Should signals transmitted to the micro-processor by any of the switches 35a–d fail to correspond to signals provided by any of the potentiometers 27 or 28, then the micro-processor generates a warning signal, so as to inform a person operating an x-ray examination apparatus in accordance with the invention that an error may have occurred and that the arrangement for imaging lead-letters is not operating reliably. An arrangement as presented in FIG. 2 having four lead-letters is particularly advantageous, because such an arrangement provides for indicating 'left' and 'right' in an anterior-to-posterior exposure by way of imaging an 'L' or an 'R', shown here attached to frame 10 as lead-letters 9a, and 9b, respectively, and such an arrangement also provided for indicating 'left' and 'right' in a posterior-to-anterior exposure by way of imaging an 'inverted L' or and 'inverted R', shown here attached to frame 11 as lead-letters 9c and 9c, respectively.

In the arrangement shown in FIG. 2 the potentiometers 27 and 28, are driven by motors 19 and 20, respectively, by means of the of belt or chain 21 together with a pulley 39 and the belt or chain 24 together with a pulley 40 respectively.

As an alternative to employing a film cassette for producing x-ray images, an x-ray image intensifier can be used as an x-ray detector. Image information generated by the x-ray image intensifier can be displayed on a monitor 41 or can be supplied to further image processing means. Whenever an x-ray image intensifier is employed for x-ray imaging, the input screen of said image intensifier constitutes the image plane wherein an x-ray image is formed. The image format displayed on the monitor depends on various adjustments of the image intensifier and e.g. also on an x-ray beam collimator which is incorporated in the x-ray source 1. By way of supplying a signal pertaining to said adjustments to a relevant potentiometer 27 and/or 28, the position of a lead-letter that is imaged during x-ray examination is suitably adapted to the actual image format of an x-ray image displayed on the monitor 41 or of an x-ray image obtained by image processing of image information generated by the x-ray image intensifier.

I claim:

1. An x-ray examination apparatus for recording patient position information in an x-ray image when the x-ray image is created, comprising:

an x-ray source and an x-ray detector defining an imaging field;

a patient receiving table for positioning a patient in said imaging field;

a supporting rail and a frame carried by said rail, said frame holding two patient position indicating x-ray absorbing markers affixed to said frame such that one or the other or neither of said markers may be selectively placed inside said imaging field between said table and said film holder by moving said frame along said rail to remotely selected positions corresponding thereto, thereby causing one or the other or neither of said patient position markers to be selectively imaged onto said x-ray detector at the same time that a patient is x-ray imaged onto said x-ray detector.

2. An x-ray examination apparatus as defined in claim 1 wherein said x-ray detector is x-ray sensitive film.

3. An x-ray examination apparatus as defined in claim 1 and further comprising at least one electrical switch for automatically sensing when said frame is in at least one predetermined position, said at least one predetermined position being where neither of said markers is in said image field.

4. An x-ray examination apparatus as defined in claim 1 and further comprising electrical drive means for moving said frame along said rail, said electrical drive means being remotely controlled from a control panel.

5. An x-ray examination apparatus for recording patient position information in an x-ray image when the x-ray image is created, comprising:
- an x-ray source and an x-ray detector defining an imaging field;
- a patient receiving table for positioning a patient in said imaging field;
- a supporting rail and a frame carried by said rail, said frame holding an x-ray absorbing marker affixed to said frame such that said marker may be selectively placed inside said imaging field between said table and said film holder by moving said frame along said rail to a remotely selected position corresponding thereto,
- thereby causing said marker to be selectively imaged or not imaged onto said x-ray detector at the same time that a patient is x-ray imaged onto said x-ray detector.

6. An x-ray examination apparatus as defined in claim 5 wherein said x-ray detector is x-ray sensitive film.

7. An x-ray examination apparatus as defined in claim 5 and further comprising at least one electrical switch for automatically sensing when said frame is in at least one predetermined position, said at least one predetermined position being where said marker is not in said image field.

8. An x-ray examination apparatus as defined in claim 5 and further comprising electrical drive means for moving said frame along said rail, said electrical drive means being remotely controlled from a control panel.

* * * * *